(12) United States Patent
Ikeda et al.

(10) Patent No.: US 10,076,236 B2
(45) Date of Patent: Sep. 18, 2018

(54) BENDING PORTION FOR ENDOSCOPE AND ENDOSCOPE

(71) Applicant: FUJIFILM Corporation, Tokyo (JP)

(72) Inventors: Toshiyuki Ikeda, Kanagawa (JP); Masatoshi Oku, Kanagawa (JP); Noriaki Uneyama, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 47 days.

(21) Appl. No.: 15/008,452

(22) Filed: Jan. 28, 2016

(65) Prior Publication Data

US 2016/0227985 A1 Aug. 11, 2016

(30) Foreign Application Priority Data

Feb. 9, 2015 (JP) ................. 2015-023236

(51) Int. Cl.
*A61B 1/005* (2006.01)
*A61B 1/008* (2006.01)
*A61B 1/00* (2006.01)
*A61B 1/04* (2006.01)

(52) U.S. Cl.
CPC ............ *A61B 1/0056* (2013.01); *A61B 1/008* (2013.01)

(58) Field of Classification Search
CPC ....... A61B 1/0056; A61B 1/008; A61B 1/005; A61B 1/0051; A61B 1/0055
See application file for complete search history.

(56) References Cited

U.S. PATENT DOCUMENTS

2002/0032371 A1* 3/2002 Torii .................... A61B 1/0052
600/142

FOREIGN PATENT DOCUMENTS

| JP | H0282936 | 3/1990 |
| JP | H0337031 | 2/1991 |
| JP | 2000-316797 | 11/2000 |
| JP | 2008-278969 | 11/2008 |
| JP | 2009-285085 | 12/2009 |
| WO | 2014024302 | 2/2014 |

OTHER PUBLICATIONS

Seki JPH02-82936, English translation from espacenet.com (7 pages).*
"Office Action of Japan Counterpart Application," dated Oct. 30, 2017,with English translation thereof, p. 1-p. 6.
"Office Action of Japan Counterpart Application," dated Jun. 1, 2018, with English translation thereof, p. 1-p. 8.

* cited by examiner

*Primary Examiner* — Timothy J Neal
(74) *Attorney, Agent, or Firm* — JCIPRNET

(57) ABSTRACT

There is provided a bending portion for an endoscope and the endoscope which can prevent the piece fall of bending pieces without enlarging the diameter of the bending portion and raising the filling rate of built-in components in the bending portion. In the bending portion, one bending piece of adjacent bending pieces is formed so that a cross-sectional shape is, for example, an elliptic shape whose major axis direction or minor axis direction corresponds to a first direction. The other bending piece of the adjacent bending pieces is formed so that a cross-sectional shape is, for example, a circular shape in which a length in the first direction differs from the first bending piece; and an abutting portion in which their end portions facing each other of the adjacent bending pieces abut on each other in at least two points when the bending portion is bent.

15 Claims, 10 Drawing Sheets

BENDING PORTION FOR ENDOSCOPE AND ENDOSCOPE

CROSS-REFERENCE TO RELATED APPLICATIONS

The patent application claims priority under 35 U.S.C. § 119 to Japanese Patent Application No. 2015-023236, filed on Feb. 9, 2015. Each of the above application(s) is hereby expressly incorporated by reference, in its entirety, into the present application.

BACKGROUND OF THE INVENTION

Field of the Invention

The present invention relates to a bending portion for an endoscope and an endoscope, and specifically relates to a bending portion for an endoscope which is formed by coupling a plurality of bending pieces in a rotatable manner, and the endoscope.

Description of the Related Art

A bending portion for an endoscope is configured by arraying a plurality of cylindrical bending pieces, which are called angle pieces or joint rings, in an axis direction of an inserting portion of the endoscope and rotatably connecting coupling leaves formed at end portions of adjacent bending pieces through a shaft such as a rivet pin.

A plurality of operation wires to perform a bending operation of the bending portion are inserted through the inside of the inserting portion of the endoscope, and these operation wires are inserted through wire receiving members provided in the bending pieces inside the bending portion. The distal end portions of these operation wires are fixed to the bending pieces arranged in the forefront of the bending portion, and the proximal end portions of these operation wires are attached to a bending operation member of a hand operating portion connected with the proximal end portion of the inserting portion. A plurality of bending pieces are rotated around a rivet pin by a push-pull operation of the operation wires by the bending operation member, and the bending portion is bent up to a position in which the end portions of adjacent bending pieces abut on each other. That is, the bending portion is designed such that the position in which the end portions of adjacent bending pieces abut on each other is in a mode in which the bending portion bends most greatly.

By the way, for example, a transnasal endoscope among endoscopes is especially requested to have a smaller outer diameter of the inserting portion and a larger diameter of a forceps channel to be inserted through the inserting portion. To meet such a request, it is forced to thin bending piece's thickness. However, when the bending piece's thickness is thinned, a phenomenon that the end portion of one bending piece gets into or onto the inside of the other bending piece because of low rigidity of the end portions of the bending pieces at the maximum bend state where the bending portion is bent most greatly, that is, a phenomenon called piece fall becomes likely to occur.

Moreover, if the end portions of adjacent bending pieces are mutually accurate circles of the same diameter, piece fall can easily occur after the end portions of the bending pieces abut on each other. When piece fall occurs, since the bending portion rapidly bends over a design value, there is a fear that built-in components such as an optical fiber, a forceps channel and a signal cable, which are inserted through the inside of the bending portion, are damaged, the decrease in durability of the bending pieces themselves is caused, and the degradation or the like of the bent shape of the bending portion is caused.

It is possible to decrease the occurrence frequency of piece fall by thickening the thickness of bending pieces, but it is not preferable because it leads to a larger diameter of the bending portion and an increase in the filling rate of built-in components under the above-mentioned request.

Therefore, the techniques of Japanese Patent Application Laid-Open Nos. 2000-316797, 2008-278969, and 2009-285085 shown below are disclosed as prevention measures of piece fall.

According to a bending portion of an endoscope disclosed in Japanese Patent Application Laid-Open No. 2000-316797, if the end edges of adjacent bending pieces do not abut on each other near the end edges of the adjacent bending pieces, piece fall is prevented by providing a projecting part, on which the end edge of one bending piece abuts, in the other bending piece. The projecting part of Japanese Patent Application Laid-Open No. 2000-316797 is provided in a belt shape along a circumferential direction on the outer peripheral surface of the bending piece.

According to a bending portion of an endoscope disclosed in Japanese Patent Application Laid-Open No. 2008-278969, piece fall is prevented by providing a projecting portion that is positioned on an axis in the bending direction of the bending portion and projects toward an inside of a bending piece, and by making projecting portions of adjacent bending pieces have different shapes from each other. As the shape of the projecting portion of Japanese Patent Application Laid-Open No. 2008-278969, for example, in the proximal-end-side end edge of a bending piece on the distal end side, there is provided a projecting portion which has a large curvature radius and projects toward the central axis, in the upper and lower portions of the outer peripheral wall at a position biased to one side across the axis line of the bending piece. Moreover, in the distal-end-side end edge of a bending piece on the proximal end side, there is provided a projecting portion which has a small curvature radius and projects toward the central axis, in the upper and lower portions of the outer peripheral wall at a position biased to the other side across the axis line of the bending piece.

According to a bending portion of an endoscope disclosed in Japanese Patent Application Laid-Open No. 2009-285085, by substantially matching the position of the proximal end portion of a distal end forming member and the position of the proximal end portion of the first bending piece in the axis direction of the inserting portion, a thick cylindrical portion is formed with the proximal end portion of the distal end forming member and the proximal end portion of the first bending piece. By this means, when an operating member (operation wire) is moved back and forth to make the bending portion perform bending operation, the proximal end surface of the thick cylindrical portion and the distal end surface of the second bending piece next to the distal end abut on each other. By this means, the piece fall of the second bending piece with respect to the first bending piece is prevented.

SUMMARY OF THE INVENTION

In the bending portion of Japanese Patent Application Laid-Open No. 2000-316797, since the belt-shaped projecting part is provided in the outer peripheral surface of the bending piece, there is a problem that the diameter of the bending piece is made larger by the projecting part. Moreover, there is also a problem that it is difficult to form the belt-shaped projecting part in the outer peripheral surface of the bending piece by press molding.

In the bending portion of Japanese Patent Application Laid-Open No. 2008-278969, since the projecting portion projects toward the inside of a bending piece, there is a problem that the filling rate of built-in components increases so as to make it difficult to reduce the diameter of the bending portion and increase the diameter of the built-in components.

As for the bending portion of Japanese Patent Application Laid-Open No. 2009-285085, as the bending portion bends more greatly, the operation wire contacts the end portion of a bending piece more strongly. By this means, in the endoscope of Japanese Patent Application Laid-Open No. 2009-285085, there are a fear that the operation force of the operation wire increases as the bending portion bends, and a fear that wear due to contact between the operation wire and the end portion of the bending piece is caused on the operation wire and the end portion of the bending piece.

The present invention is made in view of such circumferences, and aims to provide a bending portion for an endoscope and the endoscope which can prevent the piece fall of bending pieces without enlarging the diameter of a bending portion and raising the filling rate of built-in components in the bending portion.

To achieve the object of the present invention, one aspect of the present invention provides a bending portion for an endoscope, in which a plurality of bending pieces are arranged in an axis direction and adjacent bending pieces are coupled in a rotatable manner, the bending portion which is to be bent by operation of an internally inserted operation wire, comprising: a first bending piece which is one bending piece of the adjacent bending pieces and is formed so that a cross-sectional shape in a plane perpendicular to the axis direction is an elliptic shape, oval shape or flattened circular shape whose major axis direction or minor axis direction corresponds to a first direction; a second bending piece which is another bending piece of the adjacent bending pieces and is formed so that a cross-sectional shape in a plane perpendicular to the axis direction is a circular shape, elliptic shape, oval shape or flattened circular shape in which a length in the first direction differs from the first bending piece; and abutting portions in which a first end portion on a side facing the second bending piece in the first bending piece and a second end portion on a side facing the first bending piece in the second bending piece abut on each other, in at least two points when the bending portion is bent.

According to the one aspect of the present invention, at the maximum bending when the bending portion is bent, the first end portion on the side facing the second bending piece in the first bending piece and the second end portion on the side facing the first bending piece in the second bending piece abut on each other in at least two points. By this means, it is possible to prevent the piece fall of bending pieces.

That is, according to the one aspect of the present invention, by forming the first bending piece in an elliptic shape, oval shape or flattened circular shape (elongated circular shape) and forming the second bending piece in a circular shape, elliptic shape, oval shape or flattened circular shape, it is possible to prevent the piece fall of bending pieces without enlarging a diameter (outer dimension) of the bending portion and raising the filling rate of built-in components in the bending portion.

In one aspect of the present invention, it is preferable that: the first bending piece is formed so that the cross-sectional shape in the plane perpendicular to the axis direction has an elliptic shape whose major axis direction corresponds to the first direction; and the second bending piece is formed so that the cross-sectional shape in the plane perpendicular to the axis direction is an elliptic shape whose major axis direction corresponds to a second direction perpendicular to the first direction.

According to the one aspect of the present invention, it is possible to achieve the object of the present invention by combination of the first bending piece having an elliptic shape whose major axis direction corresponds to the first direction and the second bending piece having an elliptic shape whose major axis direction corresponds to the second direction perpendicular to the first direction of the first bending piece.

In one aspect of the present invention, it is preferable that the first bending piece is formed so that the cross-sectional shape in the plane perpendicular to the axis direction is an elliptic shape whose major axis direction corresponds to the first direction; and the second bending piece is formed so that the cross-sectional shape in the plane perpendicular to the axis direction is a circular shape whose diameter is shorter than a length in the first direction of the elliptic shape in the first bending piece.

According to the one aspect of the present invention, by combination of the first bending piece having an elliptic shape whose major axis direction corresponds to the first direction and the second bending piece having a circular shape whose diameter is shorter than the length in the first direction of the first bending piece, it is possible to prevent the piece fall of bending pieces without enlarging the diameter of the bending portion and raising the filling rate of built-in components in the bending portion.

In one aspect of the present invention, it is preferable that: the first bending piece is formed so that the cross-sectional shape in the plane perpendicular to the axis direction is an elliptic shape whose minor axis direction corresponds to the first direction; and the second bending piece is formed so that the cross-sectional shape in the plane perpendicular to the axis direction is a circular shape whose diameter is longer than a length in the first direction of the elliptic shape in the first bending piece.

According to the one aspect of the present invention, by combination of the first bending piece having an elliptic shape whose minor axis direction corresponds to the first direction and the second bending piece having a circular shape whose diameter is longer than the length in the first direction of the first bending piece, it is possible to prevent the piece fall of bending pieces without enlarging the diameter of the bending portion and raising the filling rate of built-in components in the bending portion.

In one aspect of the present invention, it is preferable that, one bending piece having a shorter length in the first direction in the cross-sectional shape in the plane perpendicular to the axis direction out of the first bending piece and the second bending piece, comprises a wire clearance portion configured to release the operation wire outward in a radial direction in an end portion on a side facing the other bending piece.

If a bending piece having an elliptic shape, oval shape or flattened circular shape is used, while piece fall is not caused, there is a possibility that the operation wire contacts the end portion of a bending piece positioned on the inner side, that is, a bending piece with the shorter length in the first direction. Moreover, since the curvature radius at the maximum bending is required to be reduced in the bending portion, an angle at which a bending piece rotates also increases. Therefore, since there is a case where the operation wire contacts the end portion of the one bending piece with the shorter length in the first direction, there is a possibility of causing troubles that the push-pull operation force of the operation wire increases, the bending angle of the bending portion becomes smaller than a design value and wear is caused in the operation wire, and so on.

According to the one aspect of the present invention, the one bending piece with the shorter length in the first direction is provided with the wire clearance portion which allows the operation wire to be released outward in the radial direction, in an end portion on the side facing the other bending piece. Therefore, it is possible to prevent troubles that the push-pull operation force of the operation wire increases, the bending angle of the bending portion becomes smaller than a design value and wear is caused in the operation wire, and so on.

To achieve the object of the present invention, one aspect of the present invention provides a bending portion for an endoscope, comprising: a first bending piece including a first distal end, a first proximal end, a first longitudinal axis which connects the first distal end and the first proximal end, and an outer peripheral side surface in which a proximal-end-side cross section orthogonal to the first longitudinal axis is protruding outward over a whole circumference; and a second bending piece which is coupled with a proximal end side of the first bending piece in a rotatable manner in a first direction orthogonal to the first longitudinal axis with respect to the first bending piece, the second bending piece including a second distal end, a second proximal end, a second longitudinal axis which connects the second distal end and the second proximal end, and an outer peripheral side surface in which a distal-end-side cross section orthogonal to the second longitudinal axis is protruding outward over a whole circumference, wherein, when an outer dimension in the first direction in a proximal-end-side cross section of the outer peripheral side surface of the first bending piece is R1, an outer dimension in a direction orthogonal to the first direction in the proximal-end-side cross section of the outer peripheral side surface of the first bending piece is R2, an outer dimension in the first direction in a distal-end-side cross section of the outer peripheral side surface of the second bending piece is r1 and an outer dimension in a direction orthogonal to the first direction in the distal-end-side cross section of the outer peripheral side surface of the second bending piece is r2, $(R1-r1) \times (R2-r2) < 0$ is established.

According to the one aspect of the present invention, at the maximum bending when the bending portion is bent, the first proximal end on the side facing the second bending piece in the first bending piece and the second distal end on the side facing the first bending piece in the second bending piece abut on each other in at least two points. Thus, it is possible to prevent the piece fall of bending pieces.

That is, according to the one aspect of the present invention, by satisfying $(R1-r1) \times (R2-r2) < 0$, it is possible to prevent the piece fall of bending pieces without enlarging the diameter of the bending portion and raising the filling rate of built-in components in the bending portion.

To achieve the object of the present invention, one aspect of the present invention provides an endoscope including a bending portion in which a plurality of bending pieces are arranged in an axis direction and adjacent bending pieces are coupled in a rotatable manner, the bending portion which is to be bent by operation of an internally inserted operation wire, the bending portion comprising: a first bending piece which is one bending piece of the adjacent bending pieces and is formed so that a cross-sectional shape in a plane perpendicular to the axis direction is an elliptic shape, oval shape or flattened circular shape whose major axis direction or minor axis direction corresponds to a first direction; a second bending piece which is another bending piece of the adjacent bending pieces and is formed so that a cross-sectional shape in a plane perpendicular to the axis direction is a circular shape, elliptic shape, oval shape or flattened circular shape in which a length in the first direction differs from the first bending piece; and abutting portions in which a first end portion on a side facing the second bending piece in the first bending piece and a second end portion on a side facing the first bending piece in the second bending piece abut on each other, in at least two points when the bending portion is bent.

According to one aspect of the present invention, at the maximum bending when the bending portion is bent, the first end portion on the side facing the second bending piece in the first bending piece and the second end portion on the side facing the first bending piece in the second bending piece abut on each other in at least two points. Thus, it is possible to prevent the piece fall of bending pieces.

That is, according to the one aspect of the present invention, by forming the first bending piece having an elliptic shape, oval shape or flattened circular shape (elongated circular shape) and forming the second bending piece having a circular shape, elliptic shape, oval shape or flattened circular shape, it is possible to prevent the piece fall of bending pieces without enlarging the diameter of the bending portion and raising the filling rate of built-in components in the bending portion.

To achieve the object of the present invention, one aspect of the present invention provides endoscope including a bending portion in which a plurality of bending pieces are arranged in an axis direction and adjacent bending pieces are coupled in a rotatable manner, the bending portion which is to be bent by operation of an internally inserted operation wire, the bending portion comprising: a first bending piece including a first distal end, a first proximal end, a first longitudinal axis which connects the first distal end and the first proximal end, and an outer peripheral side surface in which a proximal-end-side cross section orthogonal to the first longitudinal axis is protruding outward over a whole circumference; and a second bending piece which is coupled with a proximal end side of the first bending piece in a rotatable manner in a first direction orthogonal to the first longitudinal axis with respect to the first bending piece, the second bending piece including a second distal end, a second proximal end, a second longitudinal axis which connects the second distal end and the second proximal end, and an outer peripheral side surface in which a distal-end-side cross section orthogonal to the second longitudinal axis is protruding outward over a whole circumference, wherein, when an outer dimension in the first direction in a proximal-end-side cross section of the outer peripheral side surface of the first bending piece is R1, an outer dimension r in a direction orthogonal to the first direction in the proximal-end-side cross section of the outer peripheral side surface of the first bending piece is R2, an outer dimension in the first direction in a distal-end-side cross section of the outer peripheral side surface of the second bending piece is r1 and an outer dimension in a direction orthogonal to the first direction in the distal-end-side cross section of the outer peripheral side surface of the second bending piece is r2, $(R1-r1) \times (R2-r2) < 0$ is established.

According to the one aspect of the present invention, at the maximum bending when the bending portion is bent, the first proximal end on the side facing the second bending piece in the first bending piece and the second distal end on the side facing the first bending piece in the second bending piece abut on each other in at least two points. Thus, it is possible to prevent the piece fall of bending pieces.

That is, according to the one aspect of the present invention, by satisfying $(R1-r1) \times (R2-r2) < 0$, it is possible to prevent the piece fall of bending pieces without enlarging the diameter of the bending portion and raising the filling rate of built-in components in the bending portion.

According to a bending portion for an endoscope and an endoscope of the present invention, it is possible to prevent the piece fall of bending pieces without enlarging the diameter (outer dimension) of the bending portion and raising the filling rate of built-in components in the bending portion.

DETAILED DESCRIPTION OF THE PREFERRED EMBODIMENTS

In the following, the preferred embodiments of a bending portion for an endoscope and an endoscope according to the present invention are described in detail according to the accompanying drawings.

[Whole Configuration of Endoscope 10]

Figure 1:
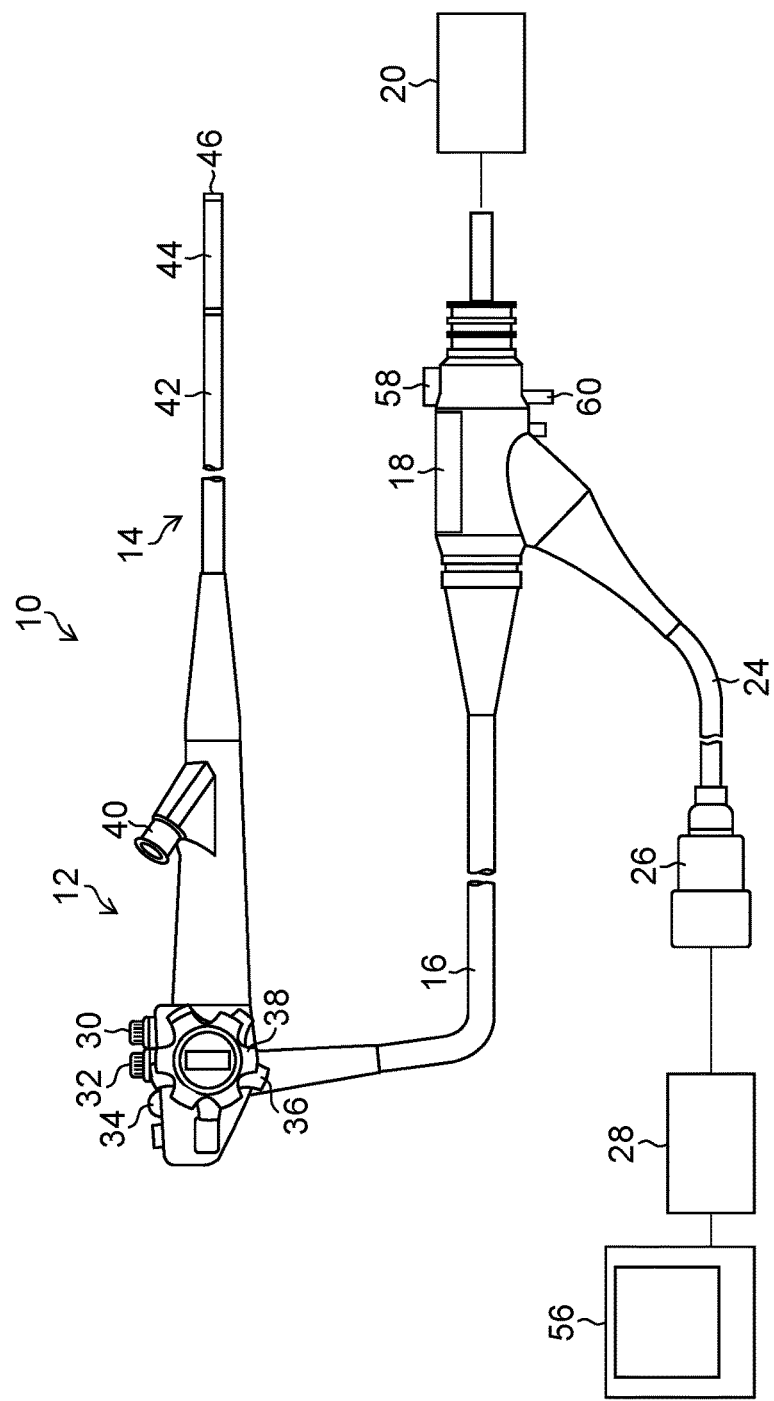
FIG. 1 is the entire configuration diagram of an endoscope to which a bending portion of an embodiment is applied.

FIG. 1 is a whole configuration diagram of the endoscope 10 of an embodiment to which a bending portion 44 of the embodiment of the present invention is applied.

The endoscope 10 includes a hand operating portion 12 held by an operator and an inserting portion 14 to be inserted into a body cavity, whose proximal end portion is coupled with the hand operating portion 12. The proximal end portion of a universal cable 16 is connected with the hand operating portion 12, and a light guide connector 18 is provided in the distal end portion of the universal cable 16. The light guide connector 18 is connected with a light source device 20, and, by this means, an illumination light is sent from the light source device 20 to illumination windows 22 and 22 (see FIG. 2) described later. Moreover, an electrical connector 26 is connected with the light guide connector 18 through a cable 24, and the electrical connector 26 is connected with a processor unit 28.

<Hand Operating Portion 12>

In the hand operating portion 12, an air-supply and water-supply button 30, a suction button 32 and a shutter button 34, which are operated by an operator, are provided in parallel and a pair of angle knobs 36 and 38 is provided. Moreover, a forceps inserting portion 40 is provided in the hand operating portion 12.

<Inserting Portion 14>

The inserting portion 14 is formed with a flexible tube portion 42, the bending portion 44 and a hard distal end portion 46 in this order from the proximal end portion toward the distal end portion. The bending portion 44 is remotely subjected to a bending operation by rotating the angle knobs 36 and 38 of the hand operating portion 12. By this means, the hard distal end portion 46 can be turned in a desired direction. The bending portion 44 is described later.

<Hard Distal End Portion 46>

Figure 2:
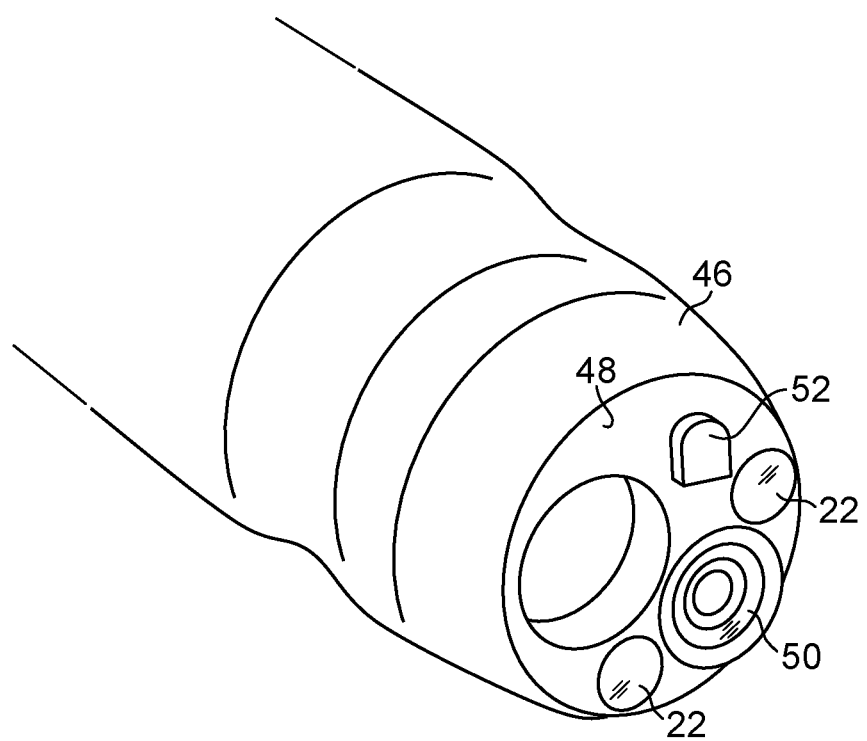
FIG. 2 is an enlarged perspective view illustrating a main part in a distal end hard portion of the endoscope illustrated in FIG. 1.

FIG. 2 is an enlarged perspective view illustrating a main part of the hard distal end portion 46.

An observation window 50, the above-mentioned illumination windows 22 and 22, an air-supply and water-supply nozzle 52 and a forceps port 54 are provided in a distal end surface 48 of the hard distal end portion 46.

An unillustrated observation optical system and imaging element are arranged on the proximal end side of the observation window 50 inside the hard distal end portion 46, and an unillustrated signal cable is connected with a substrate that supports this imaging element. The signal cable is inserted through the inserting portion 14, the hand operating portion 12, the universal cable 16 and the cable 24 in FIG. 1, extended up to the electrical connector 26 and connected with the processor unit 28. After an observation image imported from the observation window 50 in FIG. 2 is formed on the light receiving surface of the imaging element through the observation optical system and converted into an electrical signal by the imaging element, it is output to the processor unit 28 through the signal cable and converted into a video signal. By this means, the observation image is displayed on a monitor 56 connected with the processor unit 28. As an imaging element, it is possible to use a CCD (Charge Coupled Device) type image sensor and a CMOS (Complementary Metal Oxide Semiconductor) image sensor.

An emission end of an unillustrated optical fiber is arranged behind the illumination windows 22 and 22. This optical fiber is inserted through the inserting portion 14, the hand operating portion 12 and the universal cable 16 in FIG. 1 and extended up to the light guide connector 18. Therefore, when the light guide connector 18 is connected with the light source device 20, illumination light irradiated from the light source device 20 is transmitted to the illumination windows 22 and 22 in FIG. 2 through the optical fiber and irradiated forward from the illumination windows 22 and 22.

The air-supply and water-supply nozzle 52 is communicated with an unillustrated air-supply and water-supply valve operated by the air-supply and water-supply button 30 in FIG. 1. In addition, this air supply and water-supply valve is connected with a water-supply connector 58 included in the light guide connector 18 through an unillustrated tube. Unillustrated air-supply and water-supply means is connected with the water-supply connector 58, and air and water are supplied from this air-supply and water-supply means. Therefore, by operating the air-supply and water-supply button 30, it is possible to jet air or water from the air-supply and water-supply nozzle 52 in FIG. 2 toward the observation window 50.

The forceps port 54 is communicated with the forceps inserting portion 40 through an unillustrated forceps channel inserted through the inserting portion 14 in FIG. 1. Therefore, by inserting various treatment tools such as a forceps and a high-frequency knife from the forceps inserting portion 40, it is possible to introduce these treatment tools from the forceps port 54 in FIG. 2. Moreover, the forceps channel is communicated with an unillustrated suction valve operated by the suction button 32 in FIG. 1, and, furthermore, this suction valve is connected with a suction connector 60 included in the light guide connector 18 through an unillustrated tube. Therefore, by connecting an unillustrated suction pump with the suction connector 60 and operating the suction valve by the suction button 32, it is possible to suck residues and dirt, and so on, from the forceps port 54 through the forceps channel.

<Bending Portion 44>

Figure 3:
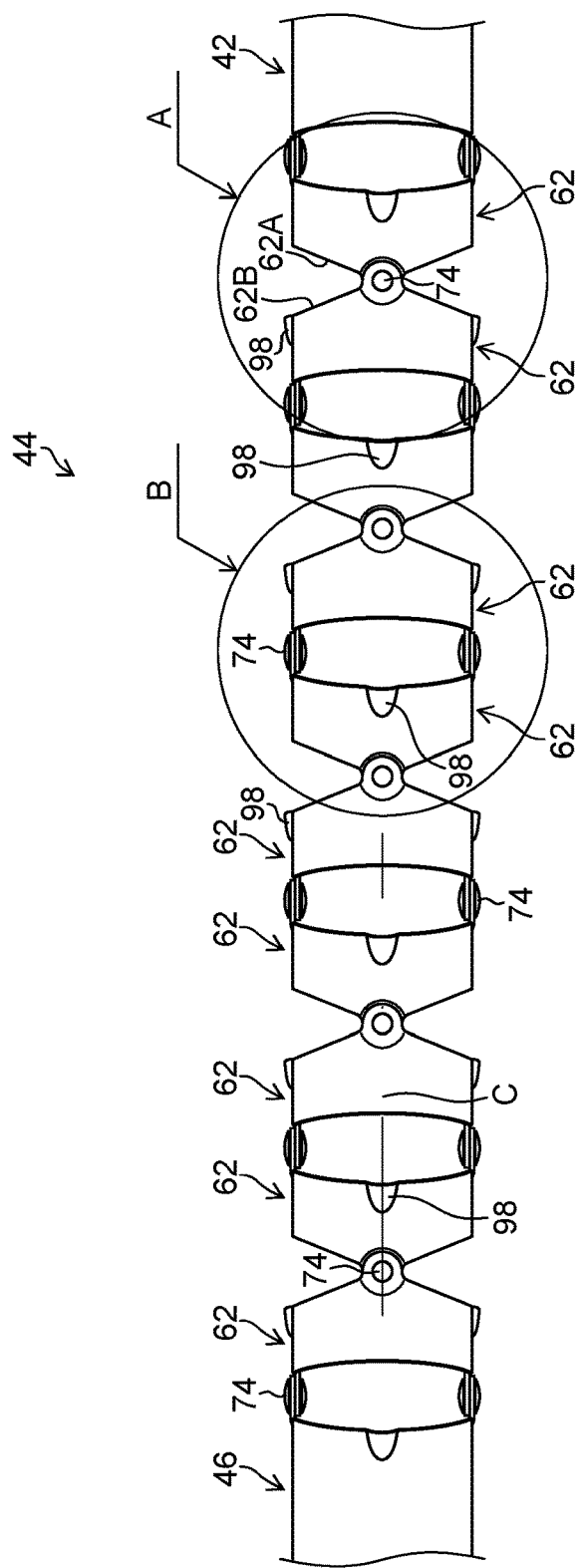
FIG. 3 is a side view illustrating a coupling mode of multiple bending pieces forming a bending portion.
Figure 4A:
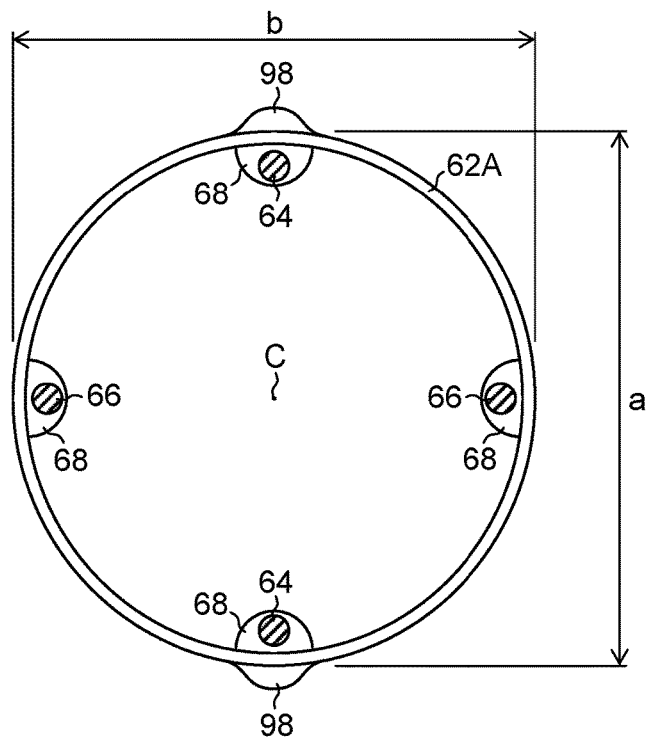
FIGS. 4A and 4B are front views of the bending pieces illustrated in FIG. 3.
Figure 4B:
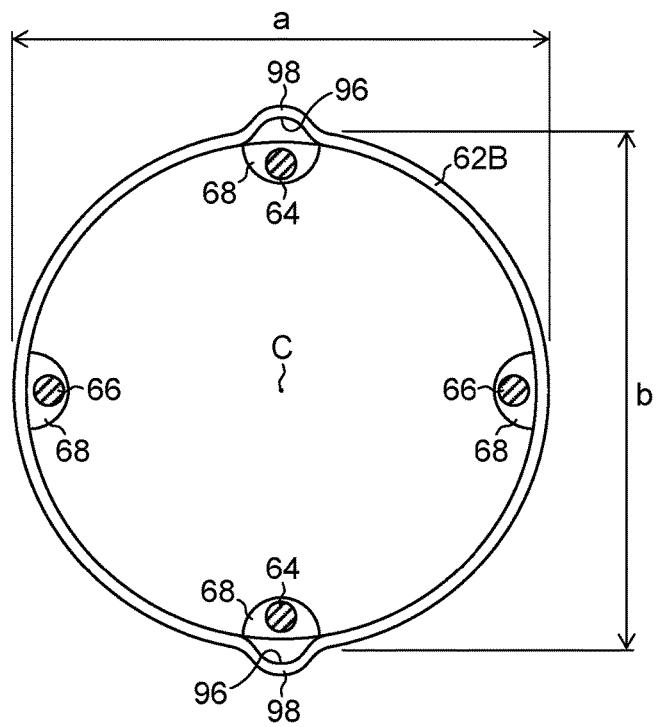
Figure 5:
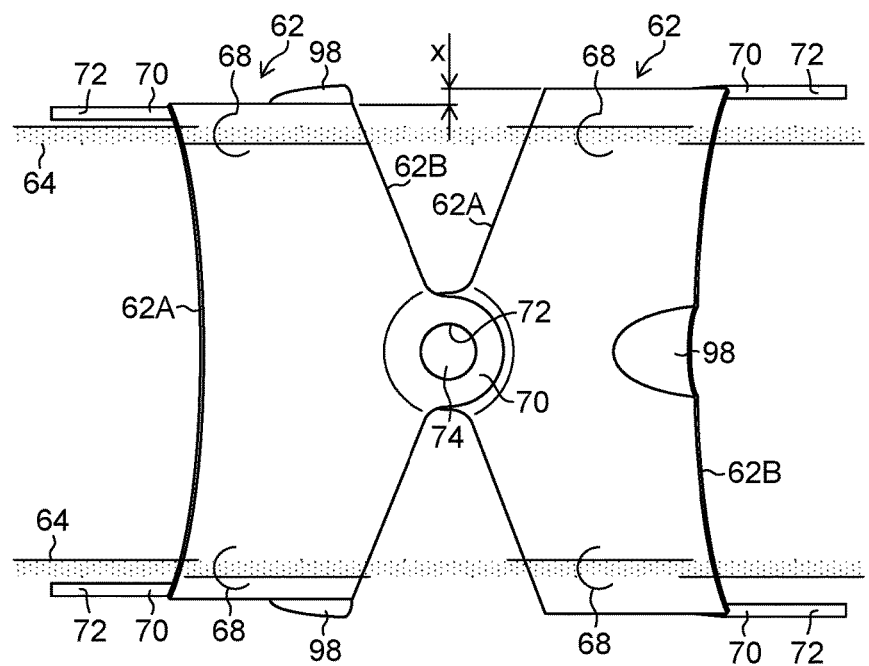
FIG. 5 is an enlarged side view of portion A in FIG. 3.
Figure 6:
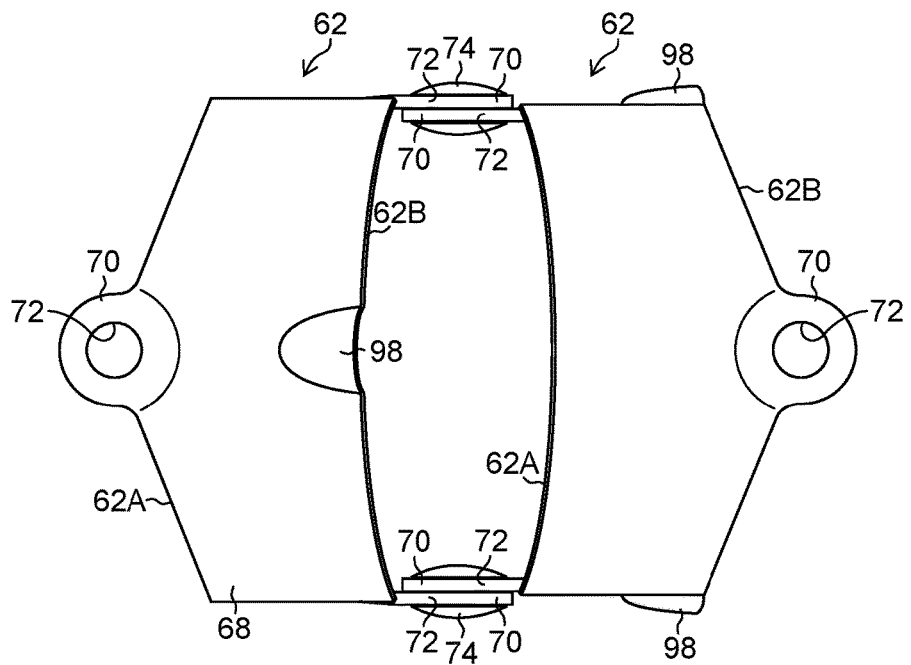
FIG. 6 is an enlarged side view of portion B in FIG. 3.

FIG. 3 is a side view illustrating a coupling mode of a plurality of bending pieces 62 forming the bending portion 44. FIG. 4A is a front view of a distal-end-side end portion 62A of a bending piece 62, and FIG. 4B is a front view of a proximal-end-side end portion 62B of the bending piece 62. Moreover, FIG. 5 is an enlarged side view of portion A of FIG. 3, and FIG. 6 is an enlarged side view of portion B of FIG. 3.

As illustrated in FIG. 3, the bending portion 44 is formed by arranging the plurality of bending pieces 62 in an axis direction C shown by the alternate long and short dash line of the bending portion 44 and coupling adjacent bending pieces 62 in a rotatable manner.

As illustrated in FIGS. 4A and 4B, the bending piece 62 is formed so that a cross-sectional shape of the bending piece 62 in a plane perpendicular to the axis direction C is an elliptic shape in which the first direction is assumed as the major axis "a" direction or the minor axis "b" direction. That is, the bending piece 62 is formed such that: a contour shape of the distal-end-side end portion 62A is an elliptical shape with major axis "a" and minor axis "b" in the up and down direction (vertical direction) and horizontal direction of FIG. 4A that is the first direction; and the contour shape of the proximal-end-side end portion 62B is an elliptical shape with major axis "a" and minor axis "b" in the horizontal direction and up and down direction of FIG. 4B. In other words, the bending piece 62 is formed in an elliptic shape in which respective contour shapes of the distal-end-side end portion 62A and the proximal-end-side end portion 62B are shifted by 90 degrees in the circumferential direction. Here, the first direction may be assumed as the horizontal direction, but an explanation is given assuming the first direction as the up and down direction on the drawing in the following explanation.

As illustrated in FIGS. 4A and 4B, inside the bending piece 62, four operation wires 64, 64, 66, and 66 of which two each are a pair are inserted at an interval of 90 degrees in the circumferential direction of the bending piece 62. Moreover, a pair of two operation wires 64 and 64 is arranged at an interval of 180 degrees, and a pair of two operation wires 66 and 66 is similarly arranged at an interval of 180 degrees. These operation wires 64, 64, 66 and 66 are inserted through cylindrical wire guide members 68 provided in the inner peripheral surface of the bending piece 62 so as to be arranged at the above-mentioned interval inside the bending portion 44.

Here, the interval to arrange the operation wires 64 and 64 or the operation wires 66 and 66 of which two are a pair is not limited to 180 degrees, and they are arranged within a range from 140 degrees to 220 degrees in association with the arrangement of built-in components, and so on.

The distal end portions of the pair of operation wires 64 and 64 are respectively fixed to the bending piece 62 arranged in the most distal end of the bending portion 44, and the proximal end portions of the pair of operation wires 64 and 64 are respectively connected with and extended to an unillustrated pulley to be rotated by the angle knob 36 illustrated in FIG. 1. By this means, when the angle knob 36 is operated to rotate the pulley, since one of the operation wires 64 and 64 in FIGS. 4A and 4B is subjected to a pull operation and the other is subjected to a push operation, the bending portion 44 is subjected to a bending operation in the up and down direction.

Moreover, the distal end portions of the pair of operation wires 66 and 66 are respectively fixed to the bending piece 62 arranged in the most distal end of the bending portion 44 in a similar manner. Further, the proximal end portions of the pair of operation wires 66 and 66 are respectively connected with and extended to an unillustrated pulley to be rotated by the angle knob 38 illustrated in FIG. 1. By this means, when the angle knob 38 is operated to rotate the pulley, since one of the operation wires 66 and 66 in FIGS. 4A and 4B is subjected to a pull-in operation and the other is subjected to a drawing-out operation, the bending portion 44 is subjected to a bending operation in the right and left direction (horizontal direction).

As illustrated in FIGS. 5 and 6, the pair of coupling leaves 70 and 70 respectively formed in a tongue-like shape (semicircular shape) are projected along the axis direction C of the bending piece 62 (see FIG. 3) in the distal-end-side end portion 62A and the proximal-end-side end portion 62B of the bending piece 62. The pair of coupling leaves 70 and 70 is arranged at an interval of 180 degrees in the circumferential direction of the bending piece 62. Moreover, the pair of coupling leaves 70 and 70 formed in the distal-end-side end portion 62A, and the pair of coupling leaves 70 and 70 formed in the proximal-end-side end portion 62B are formed in positions shifted from each other by 90 degrees in the circumferential direction of the bending piece 62.

Through-holes 72 are formed in coupling leaves 70 respectively. Each coupling leave 70 is mutually overlapped with a coupling leave 70 of an adjacent bending piece 62 such that their through-holes 72 are matched, and a rivet pin 74 is attached to the overlapped through-holes 72 and 72. By this means, the plurality of bending pieces 62 are coupled in a rotatable manner in the up and down direction through two rivet pins 74 and 74 arranged in the right and left direction, and are coupled in a rotatable manner in the right and left direction through two rivet pins 74 and 74 arranged in the up and down direction.

<Feature of Bending Piece 62>

The plurality of bending pieces 62 forming the bending portion 44 have the same structure and are formed such that the distal-end-side end portion 62A and the proximal-end-side end portion 62B have elliptic shapes as illustrated in FIGS. 4A and 4B. Moreover, the plurality of bending pieces 62 are coupled such that respective centers are matched in the axis direction C of the bending portion 44. In addition, among two adjacent bending pieces 62 and 62, they are coupled such that the distal-end-side end portion 62A of the proximal-end-side bending piece 62 which is one bending piece corresponding to the first bending piece and the proximal-end-side end portion 62B of the distal-end-side bending piece 62 which is the other bending piece corresponding to the second bending piece face to each other.

Figure 7:
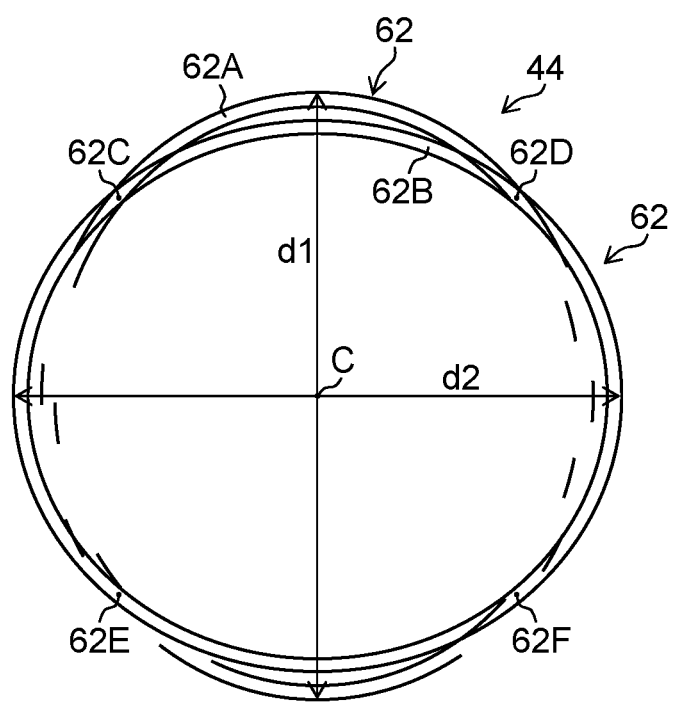
FIG. 7 is a schematic diagram of adjacent bending pieces seen from an axis direction of the bending portion.

By this means, two adjacent bending pieces 62 and 62 are coupled such that the major axis d1 of the proximal-end-side bending piece 62 shown by the alternate long and two short dashes line in FIG. 7 and the major axis d2 of the distal-end-side bending piece 62 shown by the solid line are orthogonal to each other as seen from the axis direction C of the bending portion 44 (which is the direction orthogonal to the paper surface in FIG. 7).

That is, the proximal-end-side bending piece 62 which is the first bending piece is formed so that a cross-sectional shape of the proximal-end-side bending piece 62 in a plane perpendicular to the axis direction C is an elliptic shape whose major axis direction corresponds to the first direction. Moreover, the distal-end-side bending piece 62 which is the second bending piece is formed so that a cross-sectional shape in a plane perpendicular to the axis direction C is an elliptic shape whose major axis direction corresponds to the second direction which is perpendicular to the first direction.

Therefore, the distal-end-side end portion 62A of the proximal-end-side bending piece 62 and the proximal-end-side end portion 62B of the distal-end-side bending piece 62 have different lengths in the up and down direction which is the first direction, and are coupled having a diameter difference×(=major axis "a"−minor axis "b") as illustrated in FIG. 5.

Here, FIG. 7 is a schematic diagram in which two adjacent bending pieces 62 and 62 are seen from the axis direction C of the bending portion 44, and illustrates abutting points between end portions when the two adjacent bending pieces 62 and 62 are maximally bent. Moreover, the bending piece 62 having an elliptic shape can be easily manufactured by slight bias at press molding of the coupling leaf 70. Also in this point, as compared with the bending piece of Japanese Patent Application Laid-Open No. 2000-316797 which has difficulty in press molding, the bending piece 62 of an embodiment has high utility.

[Operation of Bending Portion 44]

A) When the distal-end-side bending piece 62 is subjected to a rotation operation with respect to the proximal-end-side bending piece 62 in the upper direction centering on the major axis d2

At the maximum bending of the above-mentioned operation in which the distal-end-side end portion 62A in the proximal-end-side bending piece 62 that is the first end portion facing the distal-end-side bending piece 62 and the proximal-end-side end portion 62B in the distal-end-side bending piece 62 that is the second end portion facing the proximal-end-side bending piece 62 abut on each other, the proximal-end-side end portion 62B in the distal-end-side bending piece 62 abuts on the distal-end-side end portion 62A of the proximal-end-side bending piece 62 in at least two abutting portions 62C and 62D in positions in the proximal-end-side end portion 62B intersecting with the distal-end-side end portion 62A. Therefore, it is possible to surely prevent piece fall at the maximum bending in the upper direction.

B) When the distal-end-side bending piece 62 is subjected to a rotation operation with respect to the proximal-end-side bending piece 62 in the lower direction centering on major axis d2

At the maximum bending of the above-mentioned operation, the proximal-end-side end portion 62B of the distal-end-side bending piece 62 abuts on the distal-end-side end portion 62A of the proximal-end-side bending piece 62 in at least two abutting portions 62E and 62F in positions in the proximal-end-side end portion 62B intersecting with the distal-end-side end portion 62A. Therefore, it is possible to surely prevent piece fall at the maximum bending in the lower direction.

C) When the distal-end-side bending piece 62 is subjected to a rotation operation with respect to the proximal-end-side bending piece 62 in the left direction centering on major axis d1

At the maximum bending of the above-mentioned operation, the proximal-end-side end portion 62B of the distal-end-side bending piece 62 abuts on the distal-end-side end portion 62A of the proximal-end-side bending piece 62 in at least two abutting portions 62C and 62E in positions in the proximal-end-side end portion 62B intersecting with the distal-end-side end portion 62A. Therefore, it is possible to surely prevent piece fall at the maximum bending in the left direction.

D) When the distal-end-side bending piece 62 is subjected to a rotation operation with respect to the proximal-end-side bending piece 62 in the right direction centering on major axis d1

At the maximum bending of the above-mentioned operation, the proximal-end-side end portion 62B of the distal-end-side bending piece 62 abuts on the distal-end-side end portion 62A of the proximal-end-side bending piece 62 in at least two abutting portions 62D and 62F in positions in the proximal-end-side end portion 62B intersecting with the distal-end-side end portion 62A. Therefore, it is possible to surely prevent piece fall at the maximum bending in the right direction.

Therefore, according to the bending portion 44 of the endoscope 10 of an embodiment, it is possible to prevent the piece fall of the bending piece 62 without enlarging the diameter of the bending portion 44 and raising the filling rate of built-in components in the bending portion 44.

The coupling mode of the bending pieces 62 illustrated in FIG. 3 may be applied to all of the bending pieces 62 or may be applied to a part of the bending pieces 62. If the coupling mode is applied to a part of the bending pieces 62, the coupling mode can be applied to a plurality of bending pieces 62 in a part in which a curvature changes more greatly than other parts, that is, the plurality of bending pieces 62 arranged on the proximal end side of the bending portion 44 connected with the flexible tube portion 42.

Moreover, the shape of the bending piece 62 is not limited to an elliptic shape, and it includes a shape similar to an elliptic shape, for example, a shape such as an oval shape or a flattened circular shape (elongated circular shape). That is, the bending portion of the present invention includes: a first bending piece 62 which is one of two adjacent bending pieces 62 and 62 is formed so that a cross-sectional shape in a plane perpendicular to axis direction C is an elliptic shape, oval shape or flattened circular shape in which the first direction is the major axis direction or the minor axis direction; and a second bending piece 62 which is the other of the two adjacent bending pieces 62 and 62 is formed so that a cross-sectional shape in the plane perpendicular to axis direction C is a circular shape, elliptic shape, oval shape or flattened circular shape in which a length in the first direction is different from the first bending piece.

FIGS. 8A to 8D are schematic diagrams that describe combinations of the first bending piece 62 and the second bending piece 62 that have the above-mentioned mode.

Here, FIGS. 8A to 8D exaggerate and illustrate the shapes of the first bending piece 62 and the second bending piece 62 in the radial direction.

Figure 8A:
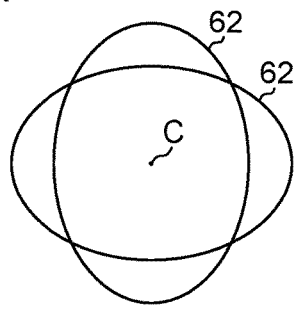
FIGS. 8A to 8D are schematic diagrams that describe a combination of the first bending piece and the second bending piece.

In FIG. 8A, the cross-sectional shape of the first bending piece 62 is an oval shape that is protruding in the up and down direction that is the first direction, and the cross-sectional shape of the second bending piece 62 is an oval shape that is protruding in the horizontal direction.

Here, the oval shapes illustrated in FIG. 8A are oval shapes of all curved lines with two orthogonal axes as symmetrical axes.

Figure 8B:
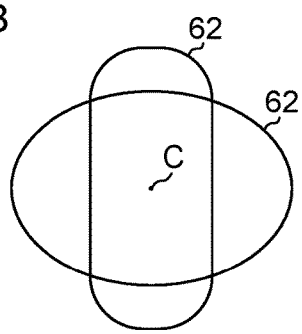

In FIG. 8B, the cross-sectional shape of the first bending piece 62 is a flattened circular shape that is protruding in the up and down direction that is the first direction, and the cross-sectional shape of the second bending piece 62 is an oval shape that is protruding in the horizontal direction.

Here, the flattened circular shape illustrated in FIG. 8B is a rounded rectangle formed with two parallel lines of equal length and two hemicycles.

Figure 8C:
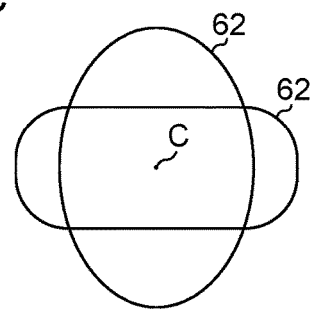

In FIG. 8C, the cross-sectional shape of the first bending piece 62 is an oval shape that is protruding in the up and down direction that is the first direction, and the cross-sectional shape of the second bending piece 62 is a flattened circular shape that is protruding in the horizontal direction.

Figure 8D:
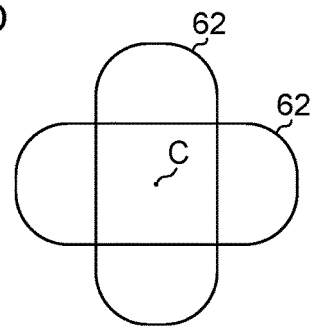

In FIG. 8D, the cross-sectional shape of the first bending piece 62 is a flattened circular shape that is protruding in the up and down direction that is the first direction, and the cross-sectional shape of the second bending piece 62 is a flattened circular shape that is protruding in the horizontal direction.

Even by the combination of FIGS. 8A to 8D, it is possible to obtain an effect similar to the combination of the bending pieces 62 and 62 illustrated in FIG. 7.

[Modified Example of Bending Portion 44A]

Figure 9:
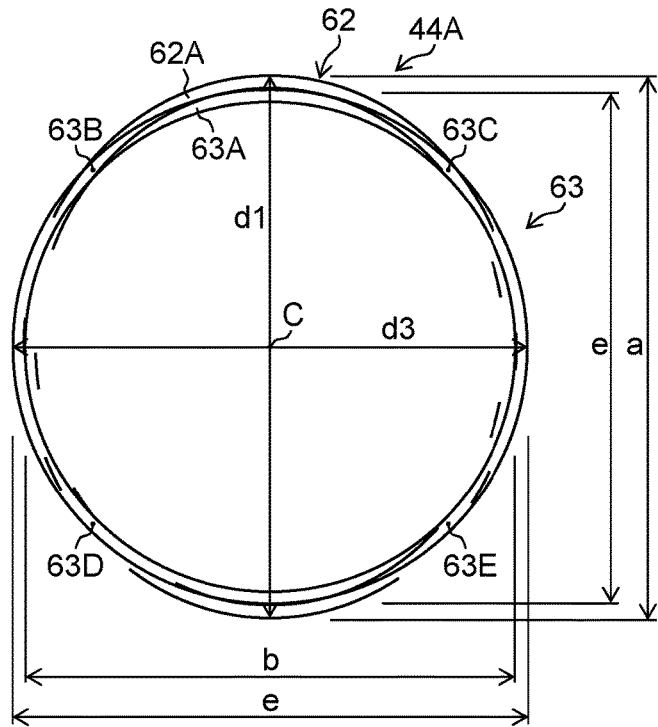
FIG. 9 is an explanatory drawing illustrating a modified example of a bending portion of an embodiment.

FIG. 9 illustrates the bending portion 44A as a modified example of the embodiment. According to FIG. 9, the proximal-end-side bending piece 62 which is the first bending piece shown by an alternate long and two short dashes line is formed so that the cross-sectional shape in a plane perpendicular to the axis direction C of the proximal-end-side bending piece 62 is an ellipse shape in which the first direction corresponds to a major axis direction. Moreover, the distal-end-side bending piece 63 which is the second bending piece shown by a solid line is formed so that the cross-sectional shape of the distal-end-side bending piece 63 in the plane perpendicular to the axis direction C is a circular shape whose diameter is shorter than a length in the first direction of the elliptic shape in the proximal-end-side bending piece 62.

The bending pieces 62 and 63 are coupled in a rotatable manner in the up and down direction and the right and left direction through an unillustrated coupling leaves such that respective central axes are matched. Moreover, there is a diameter difference between the bending piece 62 and the bending piece 63. That is, a diameter "e" of the bending piece 63 is smaller than a major axis "a" of the bending piece 62 and larger than a minor axis "b" of the bending piece 62. In addition, FIG. 9 illustrates abutting portions of end portions at the maximum bending of two adjacent bending pieces 62 and 63. [Operation of bending portion 44A]

A) When the distal-end-side bending piece 63 is subjected to a rotation operation with respect to the proximal-end-side bending piece 62 in the upper direction centering on a diametric axis d3 of the bending piece 63

At the maximum bending of the above-mentioned operation, the proximal-end-side end portion 63A of the distal-end-side bending piece 63 abuts on the distal-end-side end portion 62A of the proximal-end-side bending piece 62 in at least two abutting portions 63B and 63C in positions in the proximal-end-side end portion 63A intersecting with the distal-end-side end portion 62A. Therefore, it is possible to surely prevent piece fall at the maximum bending in the upper direction.

B) When the distal-end-side bending piece 63 is subjected to a rotation operation with respect to the proximal-end-side bending piece 62 in the lower direction centering on the diametric axis d3

At the maximum bending of the above-mentioned operation, the proximal-end-side end portion 63A of the distal-end-side bending piece 63 abuts on the distal-end-side end portion 62A of the proximal-end-side bending piece 62 in at least two abutting portions 63D and 63E in positions in the proximal-end-side end portion 63A intersecting with the distal-end-side end portion 62A. Therefore, it is possible to surely prevent piece fall at the maximum bending in the lower direction.

C) When the distal-end-side bending piece 63 is subjected to a rotation operation with respect to the proximal-end-side bending piece 62 in the left direction centering on a major axis d1

At the maximum bending of the above-mentioned operation, the proximal-end-side end portion 63A of the distal-end-side bending piece 63 abuts on the distal-end-side end portion 62A of the proximal-end-side bending piece 62 in at least two abutting portions 63B and 63D in positions in the proximal-end-side end portion 63A intersecting with the distal-end-side end portion 62A. Therefore, it is possible to surely prevent piece fall at the maximum bending in the left direction.

D) When the distal-end-side bending piece 63 is subjected to a rotation operation with respect to the proximal-end-side bending piece 62 in the right direction centering on the major axis d1

At the maximum bending of the above-mentioned operation, the proximal-end-side end portion 63A of the distal-end-side bending piece 63 abuts on the distal-end-side end portion 62A of the proximal-end-side bending piece 62 in at least two abutting portions 63C and 63E in positions in the proximal-end-side end portion 63A intersecting with the distal-end-side end portion 62A. Therefore, it is possible to surely prevent piece fall at the maximum bending in the right direction.

Therefore, according to the bending portion 44A of the embodiment, it is possible to prevent the piece fall of the bending pieces 62 and 63 without enlarging the diameter of the bending portion 44A and raising the filling rate of built-in components in the bending portion 44.

[Modified Example of Bending Portion 44B]

Figure 10:
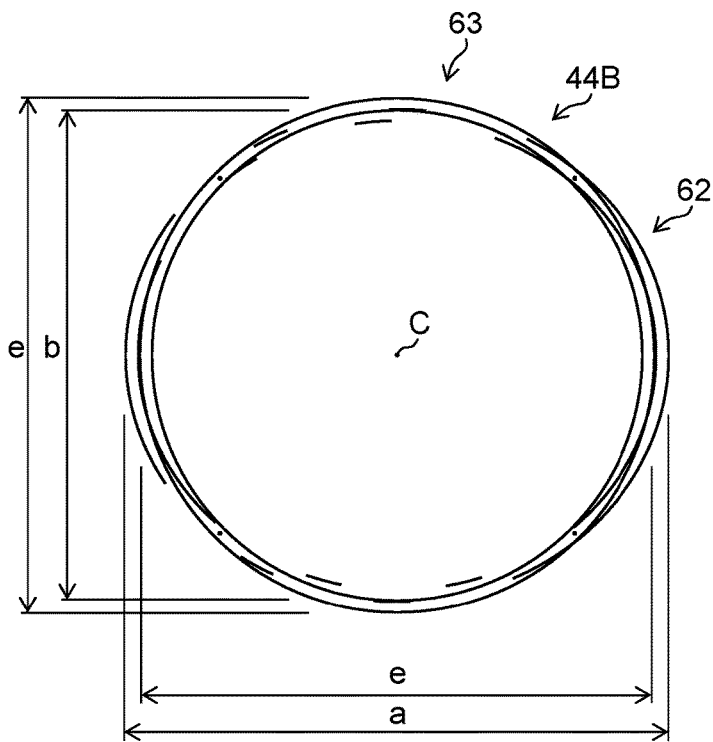
FIG. 10 is an explanatory drawing illustrating a modified example of a bending portion of an embodiment.

FIG. 10 illustrates the bending portion 44B as a modified example of the embodiment. According to FIG. 10, the proximal-end-side bending piece 62 which is the first bending piece shown by an alternate long and two short dashes line is formed so that a cross-sectional shape of the proximal-end-side bending piece 62 in a plane perpendicular to the axis direction C is an elliptic shape whose minor axis direction corresponds to the up and down direction that is the first direction. Moreover, the distal-end-side bending piece 63 which is the second bending piece shown by a solid line is formed so that a cross-sectional shape of the distal-end-side bending piece 63 in the plane perpendicular to the axis direction C is a circular shape whose diameter is longer than a length in the first direction of the elliptic shape in the proximal-end-side bending piece 62.

That is, the bending portion 44B of FIG. 10 corresponds to a mode in which the bending portion 44A illustrated in FIG. 9 is rotated by 90 degrees in the circumferential direction of the bending pieces 62 and 63. Therefore, also in the bending portion 44B of FIG. 10, it is possible to obtain effects similar to the bending portion 44A in FIG. 9.

[Another Definition of the Present Invention]

If the present invention is seen from a different angle, it can be defined as follows.

Figure 11A:
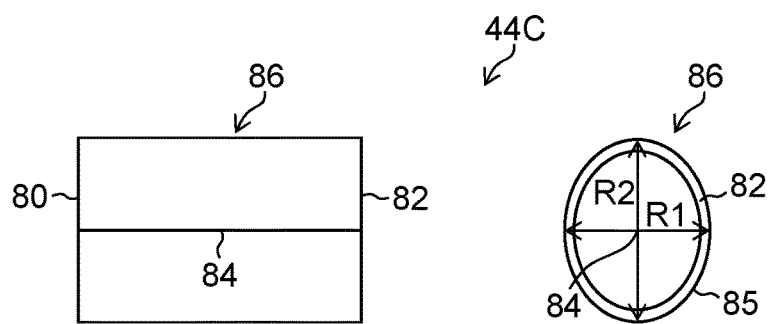
FIGS. 11A and 11B are explanatory drawings of a bending portion for describing another definition of the present invention.
Figure 11B:
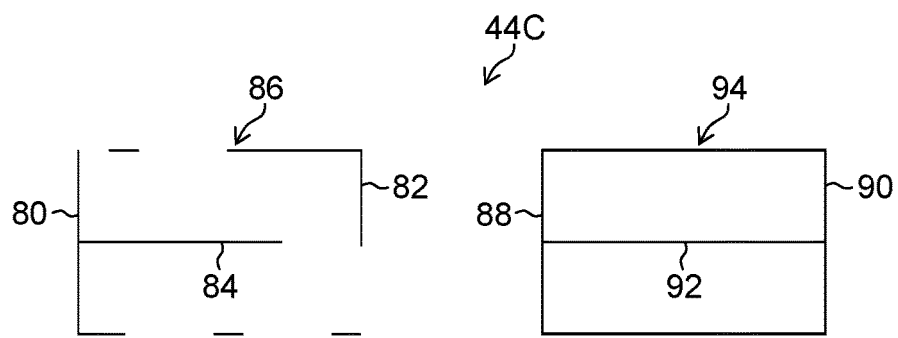
Figure 11B:
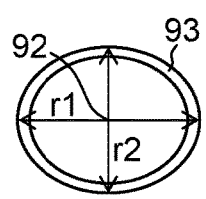

FIGS. 11A and 11B illustrate a bending portion 44C to describe the above-mentioned definition. The bending portion 44C is configured by alternately coupling first bending pieces 86 and second bending pieces 94.

As illustrated in FIG. 11A, a first bending piece 86 includes: a first distal end 80; a first proximal end 82; a first longitudinal axis 84 which connects the first distal end 80 and the first proximal end 82; and an outer peripheral side surface 85 in which a proximal-end-side cross section orthogonal to the first longitudinal axis 84 is protruding outward over the whole circumference (in other words, the proximal-end-side cross section has a shape expanding (swelling) from the inner side toward the outer side). Specifically, examples of the proximal-end-side cross sectional shape orthogonal to the first longitudinal axis 84 include an elliptic shape, oval shape, flattened circular shape and elongated circular shape.

Moreover, the second bending piece 94 is coupled with the proximal end side of the first bending piece 86 in a manner rotatable in a first direction orthogonal to the first longitudinal axis 84 with respect to the first bending piece 86. As illustrated in FIG. 11B, the second bending piece 94 includes: a second distal end 88; a second proximal end 90; a second longitudinal axis 92 which connects the second distal end 88 and the second proximal end 90; and an outer peripheral side surface 93 in which a distal-end-side cross section orthogonal to the second longitudinal axis 92 is protruding outward over the whole circumference (in other words, the distal-end-side cross section has a shape expanding (swelling) from the inner side toward the outer side). Specifically, examples of the distal-end-side cross sectional shape orthogonal to the second longitudinal axis 92 include a circular shape, elliptic shape, oval shape, flattened circular shape and elongated circular shape.

Further, according to the bending portion 44C, when the diameter (outer dimension) in the first direction in the proximal-end-side cross section of the outer peripheral side surface 85 of the first bending piece 86 is R1, the diameter (outer dimension) in a direction orthogonal to the first direction in the proximal-end-side cross section of the outer peripheral side surface 85 of the first bending piece 86 is R2, the diameter (outer dimension) in the first direction in the distal-end-side cross section of the outer peripheral side surface 93 of the second bending piece 94 is r1, and the diameter (outer dimension) in a direction orthogonal to the first direction in the distal-end-side cross section of the outer peripheral side surface 93 of the second bending piece 94 is r2, $(R1-r1) \times (R2-r2) < 0$ is established. That is, the diameters of the first bending piece 86 and the second bending piece 94 are respectively set such that $(R1-r1)$ or $(R2-r2)$ becomes a negative value.

According to the bending portion 44C, at the maximum bending when the bending portion 44C is subjected to a bending operation, the first proximal end 82 on the side facing the second bending piece 94 in the first bending piece 86 and the second distal end 88 on the side facing the first bending piece 86 in the second bending piece 94 abut on each other in at least two abutting portions. By this means, it is possible to prevent the piece fall of the first bending piece 86 and the second bending piece 94.

That is, according to the bending portion 44C, by satisfying $(R1-r1) \times (R2-r2) < 0$, it is possible to prevent the piece fall of the bending pieces 86 and 94 without enlarging the diameter of the bending portion 44C and raising the filling rate of built-in components in the bending portion 44C.

[Other Features of Bending Portion 44]

Figure 12:
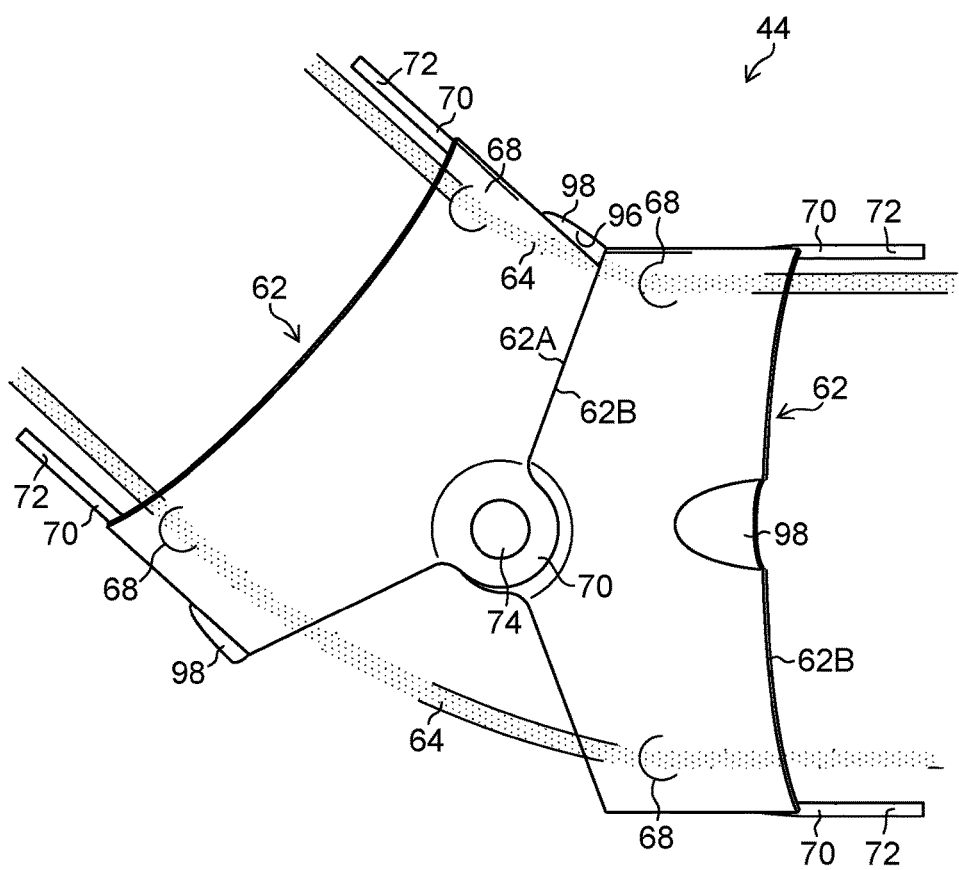
FIG. 12 is an enlarged side view illustrating a main part of the bending portion where an operation wire is inserted through a wire clearance portion provided in the bending piece.

FIG. 12 is an enlarged side view of a main part of the bending portion 44, which illustrates a state where operation wires 64 pass through wire clearance portions 96 provided in the bending piece 62 at the maximum bending of the bending portion 44.

If the bending pieces 62 having the elliptic shape, oval shape or flattened circular shape are used, while piece fall is not caused, there is a possibility that the operation wire 64 contacts the end portion of a bending piece positioned inside of the other bending piece, in other words, contacts the proximal-end-side end portion 62B of the distal-end-side bending piece 62 which is one bending piece with the shorter length in the first direction than the other.

Moreover, since the curvature radius at the maximum bending is required to be reduced in the bending portion 44, an angle at which the bending piece 62 rotates also increases. Therefore, since there is a case where the operation wire 64 contacts the proximal-end-side end portion 62B of the distal-end-side bending piece 62 with the shorter length in the first direction, there is a fear of causing troubles that the push-pull operation force of the operation wire 64 increases, the bending angle of the bending portion 44 becomes smaller than a design value and wear is caused in the proximal-end-side end portion 62B and the operation wire 64, and so on.

Then, according to the bending portion 44 in FIG. 12, the wire clearance portions 96 which allow the operation wires 64 to escape outward in the radial direction are formed in the proximal-end-side end portion 62B of the distal-end-side bending piece 62 with the shorter length in the first direction, which is the proximal-end-side end portion 62B on the side facing the proximal-end-side bending piece 62 which is the other bending piece.

That is, to prevent the operation wire 64 from contacting the end portion of the bending piece 62 at the maximum bending of the bending portion 44, the wire clearance portions 96 having recessed shapes or groove shapes when viewing from inside of the bending piece 62, are provided in operation wire insertion portions of the end portion of a bending piece that comes inner side of the curvature when the end portions of bending pieces abut on each other, out of portions to which the operation wires 64 are highly likely to contact.

By this means, it is possible to prevent troubles that the push-pull operation force of the operation wire 64 increases, the bending angle of the bending portion 44 becomes smaller than a design value and wear is caused in the operation wire 64, and so on.

Specifically, as illustrated in FIG. 4B, the wire clearance portions 96 are provided in the inner peripheral surface of the top portion of the minor axis as a concave shape or groove shape. The wire clearance portion 96 is formed by press molding the proximal-end-side end portion 62B of the bending piece 62, by this means, a projecting part 98 is formed in the outer peripheral surface of the bending piece 62 corresponding to the wire clearance portion 96. Since the projecting part 98 abuts on the distal-end-side end portion 62A of the proximal-end-side bending piece 62 at the maximum bending of the bending portion 44, it is possible to prevent sinking and overriding of the end portions of adjacent bending pieces 62 and 62. Moreover, abutting portions at the maximum bending are three points including the projecting part 98.

The reasons for forming the wire clearance portions 96 in the proximal-end-side end portion 62B of the distal-end-side bending piece 62 are as follows. Since the proximal-end-side end portion 62B is pressed in the right and left direction from outside in an outer peripheral concavity and is subjected to slight diameter expansion (deformation) in the up and down direction at the time of press molding of the coupling leaves 70 (see FIGS. 5 and 6) which are coupling members, it is not necessary to allow the operation wire to be released. Since the distal-end-side end portion 62A is pressed in the right and left direction from inside in the outer peripheral convexity and is subjected to slight diameter reduction (deformation) in the up and down direction, the operation wire 64 is caused to contact the bending piece 62. Moreover, since a movement amount of the operation wire 64 in the proximal-end-side end portion 62B is larger than that in the distal-end-side end portion 62A and a contact range thereof is also wider, wear is likely to progress in the proximal-end-side end portion 62B.

Moreover, the wire clearance portion 96 may be provided in at least the bending piece 62 with the largest contact angle among the plurality of bending pieces 62 forming the bending portion 44. The reason is that the operation wire 64 has an acute angle and a contact resistance is large in the proximal end portion of such the bending piece 62.

Here, naturally, the wire clearance portions 96 to allow the operation wire 64 to escape are provided in the proximal-end-side end portion 62B of the distal-end-side bending piece 62 with the shorter length in the first direction.

The bending portion according to an embodiment has been described above in detail, but the present invention is not limited to the above-mentioned examples, and it should be understood that various improvements and modifications may be made without departing from the gist of the present invention.

What is claimed is:

1. A bending portion for an endoscope, in which a plurality of bending pieces are arranged in an axis direction and adjacent bending pieces are coupled in a rotatable manner, the bending portion which is to be bent by operation of an internally inserted operation wire, comprising:
   a first bending piece which is one bending piece of the adjacent bending pieces and is formed so that a cross-sectional shape in a plane perpendicular to the axis direction is an elliptic shape, oval shape or flattened circular shape whose major axis direction or minor axis direction corresponds to a first direction;
   a second bending piece which is another bending piece of the adjacent bending pieces and is formed so that a cross-sectional shape in a plane perpendicular to the axis direction is a circular shape, elliptic shape, oval shape or flattened circular shape in which a length in the first direction differs from the first bending piece; and
   abutting portions in which a first end portion on a side facing the second bending piece in the first bending piece and a second end portion on a side facing the first bending piece in the second bending piece abut on each other, in at least two points when the bending portion is bent when the first bending piece rotates around a rotating axis orthogonal to the first direction with respect to the second bending piece by bending operation of the bending portion, wherein:
   the first bending piece is formed so that the cross-sectional shape in the plane perpendicular to the axis direction is an elliptic shape whose major axis direction corresponds to the first direction; and
   the second bending piece is formed so that the cross-sectional shape in the plane perpendicular to the axis direction is a circular shape whose diameter is shorter than a length in the first direction of the elliptic shape in the first bending piece.

2. The bending portion for an endoscope according to claim 1, wherein,
   one bending piece having a shorter length in the first direction in the cross-sectional shape in the plane perpendicular to the axis direction out of the first bending piece and the second bending piece, comprises a wire clearance portion configured to release the operation wire outward in a radial direction in an end portion on a side facing the other bending piece.

3. A bending portion for an endoscope, in which a plurality of bending pieces are arranged in an axis direction and adjacent bending pieces are coupled in a rotatable manner, the bending portion which is to be bent by operation of an internally inserted operation wire, comprising:
   a first bending piece which is one bending piece of the adjacent bending pieces and is formed so that a cross-sectional shape in a plane perpendicular to the axis direction is an elliptic shape, oval shape or flattened circular shape whose major axis direction or minor axis direction corresponds to a first direction;
   a second bending piece which is another bending piece of the adjacent bending pieces and is formed so that a cross-sectional shape in a plane perpendicular to the axis direction is a circular shape, elliptic shape, oval shape or flattened circular shape in which a length in the first direction differs from the first bending piece; and
   abutting portions in which a first end portion on a side facing the second bending piece in the first bending piece and a second end portion on a side facing the first bending piece in the second bending piece abut on each other, in at least two points when the bending portion is bent when the first bending piece rotates around a rotating axis orthogonal to the first direction with respect to the second bending piece by bending operation of the bending portion, wherein:
   the first bending piece is formed so that the cross-sectional shape in the plane perpendicular to the axis direction is an elliptic shape whose minor axis direction corresponds to the first direction; and
   the second bending piece is formed so that the cross-sectional shape in the plane perpendicular to the axis direction is a circular shape whose diameter is longer than a length in the first direction of the elliptic shape in the first bending piece.

4. A bending portion for an endoscope, comprising:
   a first bending piece including a first distal end, a first proximal end, a first longitudinal axis which connects the first distal end and the first proximal end, and an outer peripheral side surface in which a proximal-end-side cross section orthogonal to the first longitudinal axis is protruding outward over a whole circumference; and
   a second bending piece which is coupled with a proximal end side of the first bending piece in a rotatable manner in a first direction orthogonal to the first longitudinal axis with respect to the first bending piece, the second bending piece including a second distal end, a second proximal end, a second longitudinal axis which connects the second distal end and the second proximal end, and an outer peripheral side surface in which a distal-end-side cross section orthogonal to the second longitudinal axis is protruding outward over a whole circumference, wherein, an outer dimension in the first direction in a proximal-end-side cross section of the outer peripheral side surface of the first bending piece is R1, an outer dimension in a direction orthogonal to the first direction in the proximal-end-side cross section of the outer peripheral side surface of the first bending piece is R2, an outer dimension in the first direction in a distal-end-side cross section of the outer peripheral side surface of the second bending piece is r1 and an outer dimension in a direction orthogonal to the first direction in the distal-end-side cross section of the outer peripheral side surface of the second bending piece is r2, (R1−r1)×(R2−r2)<0, wherein a shape of the proximal-end-side cross section orthogonal to the first longitudinal axis includes an elliptic shape, oval shape and elongated circular shape, and a shape of distal-end-side cross section orthogonal to the second longitudinal axis includes an elliptic shape, oval shape and elongated circular shape, wherein the shape of the proximal-end-side cross section orthogonal to the first longitudinal axis and the shape of distal-end-side cross section orthogonal to the second longitudinal axis are different.

5. An endoscope including a bending portion in which a plurality of bending pieces are arranged in an axis direction and adjacent bending pieces are coupled in a rotatable manner, the bending portion which is to be bent by operation of an internally inserted operation wire, the bending portion comprising:

a first bending piece which is one bending piece of the adjacent bending pieces and is formed so that a cross-sectional shape in a plane perpendicular to the axis direction is an elliptic shape, oval shape or flattened circular shape whose major axis direction or minor axis direction corresponds to a first direction;

a second bending piece which is another bending piece of the adjacent bending pieces and is formed so that a cross-sectional shape in a plane perpendicular to the axis direction is a circular shape, elliptic shape, oval shape or flattened circular shape in which a length in the first direction differs from the first bending piece; and abutting portions in which a first end portion on a side facing the second bending piece in the first bending piece and a second end portion on a side facing the first bending piece in the second bending piece abut on each other, in at least two points when the bending portion is bent when the first bending piece rotates around a rotating axis orthogonal to the first direction with respect to the second bending piece by bending operation of the bending portion, wherein:

the first bending piece is formed so that the cross-sectional shape in the plane perpendicular to the axis direction is an elliptic shape whose major axis direction corresponds to the first direction; and the second bending piece is formed so that the cross-sectional shape in the plane perpendicular to the axis direction is a circular shape whose diameter is shorter than a length in the first direction of the elliptic shape in the first bending piece.

6. An endoscope including a bending portion in which a plurality of bending pieces are arranged in an axis direction and adjacent bending pieces are coupled in a rotatable manner, the bending portion which is to be bent by operation of an internally inserted operation wire, the bending portion comprising:

a first bending piece including a first distal end, a first proximal end, a first longitudinal axis which connects the first distal end and the first proximal end, and an outer peripheral side surface in which a proximal-end-side cross section orthogonal to the first longitudinal axis is protruding outward over a whole circumference; and a second bending piece which is coupled with a proximal end side of the first bending piece in a rotatable manner in a first direction orthogonal to the first longitudinal axis with respect to the first bending piece, the second bending piece including a second distal end, a second proximal end, a second longitudinal axis which connects the second distal end and the second proximal end, and an outer peripheral side surface in which a distal-end-side cross section orthogonal to the second longitudinal axis is protruding outward over a whole circumference, wherein, an outer dimension in the first direction in a proximal-end-side cross section of the outer peripheral side surface of the first bending piece is R1, an outer dimension r in a direction orthogonal to the first direction in the proximal-end-side cross section of the outer peripheral side surface of the first bending piece is R2, an outer dimension in the first direction in a distal-end-side cross section of the outer peripheral side surface of the second bending piece is r1 and an outer dimension in a direction orthogonal to the first direction in the distal-end-side cross section of the outer peripheral side surface of the second bending piece is r2, (R1−r1)×(R2−r2)<0, wherein a shape of the proximal-end-side cross section orthogonal to the first longitudinal axis includes an elliptic shape, oval shape and elongated circular shape, and a shape of distal-end-side cross section orthogonal to the second longitudinal axis includes an elliptic shape, oval shape and elongated circular shape, wherein the shape of the proximal-end-side cross section orthogonal to the first longitudinal axis and the shape of distal-end-side cross section orthogonal to the second longitudinal axis are different.

7. A bending portion for an endoscope, in which a plurality of bending pieces are arranged in an axis direction and adjacent bending pieces are coupled in a rotatable manner, the bending portion which is to be bent by operation of an internally inserted operation wire, comprising:

a first bending piece which is one bending piece of the adjacent bending pieces and is formed so that a cross-sectional shape in a plane perpendicular to the axis direction is an elliptic shape, oval shape or flattened circular shape whose major axis direction or minor axis direction corresponds to a first direction;

a second bending piece which is another bending piece of the adjacent bending pieces and is formed so that a cross-sectional shape in a plane perpendicular to the axis direction is a circular shape, elliptic shape, oval shape or flattened circular shape in which a length in the first direction differs from the first bending piece; and abutting portions in which a first end portion on a side facing the second bending piece in the first bending piece and a second end portion on a side facing the first bending piece in the second bending piece abut on each other, in at least two points when the bending portion is bent, wherein, one bending piece having a shorter length in the first direction in the cross-sectional shape in the plane perpendicular to the axis direction out of the first bending piece and the second bending piece, comprises a wire clearance portion formed in an inner peripheral surface of the bending piece of a top portion of the minor axis of the bending piece and configured to release the operation wire outward in a radial direction in an end portion on a side facing the other bending piece.

8. An endoscope including a bending portion in which a plurality of bending pieces are arranged in an axis direction and adjacent bending pieces are coupled in a rotatable manner, the bending portion which is to be bent by operation of an internally inserted operation wire, the bending portion comprising:

a first bending piece which is one bending piece of the adjacent bending pieces and is formed so that a cross-sectional shape in a plane perpendicular to the axis direction is an elliptic shape, oval shape or flattened circular shape whose major axis direction or minor axis direction corresponds to a first direction;

a second bending piece which is another bending piece of the adjacent bending pieces and is formed so that a cross-sectional shape in a plane perpendicular to the axis direction is a circular shape, elliptic shape, oval shape or flattened circular shape in which a length in the first direction differs from the first bending piece; and abutting portions in which a first end portion on a side facing the second bending piece in the first bending piece and a second end portion on a side facing the first bending piece in the second bending piece abut on each other, in at least two points when the bending portion is bent, wherein, one bending piece having a shorter length in the first direction in the cross-sectional shape in the plane perpendicular to the axis direction out of the first bending piece and the second bending piece, comprises a wire clearance portion formed in an inner peripheral surface of the bending piece of a top portion of the minor axis of the bending piece and configured to release the operation wire outward in a radial direction in an end portion on a side facing the other bending piece.

9. A bending portion for an endoscope, in which a plurality of bending pieces are arranged in an axis direction and adjacent bending pieces are coupled in a rotatable manner, the bending portion which is to be bent by operation of an internally inserted operation wire, comprising:

a first bending piece which is one bending piece of the adjacent bending pieces and is formed so that a cross-sectional shape in a plane perpendicular to the axis direction is an elliptic shape, oval shape or flattened circular shape whose major axis direction or minor axis direction corresponds to a first direction;

a second bending piece which is another bending piece of the adjacent bending pieces and is formed so that a cross-sectional shape in a plane perpendicular to the axis direction is a circular shape in which a length in the first direction differs from the first bending piece; and abutting portions in which a first end portion on a side facing the second bending piece in the first bending piece and a second end portion on a side facing the first bending piece in the second bending piece abut on each other, in at least two points when the bending portion is bent.

10. An endoscope including a bending portion in which a plurality of bending pieces are arranged in an axis direction and adjacent bending pieces are coupled in a rotatable manner, the bending portion which is to be bent by operation of an internally inserted operation wire, the bending portion comprising:

a first bending piece which is one bending piece of the adjacent bending pieces and is formed so that a cross-sectional shape in a plane perpendicular to the axis direction is an elliptic shape, oval shape or flattened circular shape whose major axis direction or minor axis direction corresponds to a first direction;

a second bending piece which is another bending piece of the adjacent bending pieces and is formed so that a cross-sectional shape in a plane perpendicular to the axis direction is a circular shape in which a length in the first direction differs from the first bending piece; and abutting portions in which a first end portion on a side facing the second bending piece in the first bending piece and a second end portion on a side facing the first bending piece in the second bending piece abut on each other, in at least two points when the bending portion is bent.

11. A bending portion for an endoscope, comprising:

a first bending piece including a first distal end, a first proximal end, a first longitudinal axis which connects the first distal end and the first proximal end, and an outer peripheral side surface in which a proximal-end-side cross section orthogonal to the first longitudinal axis is protruding outward over a whole circumference;

a second bending piece which is coupled with a proximal end side of the first bending piece in a rotatable manner in a first direction orthogonal to the first longitudinal axis with respect to the first bending piece, the second bending piece including a second distal end, a second proximal end, a second longitudinal axis which connects the second distal end and the second proximal end, and an outer peripheral side surface in which a distal-end-side cross section orthogonal to the second longitudinal axis is protruding outward over a whole circumference; and a wire clearance portion formed at least in the proximal end side of the bending piece with a largest contact angle among the first bending piece and the second bending piece, wherein, an outer dimension in the first direction in a proximal-end-side cross section of the outer peripheral side surface of the first bending piece is R1, an outer dimension in a direction orthogonal to the first direction in the proximal-end-side cross section of the outer peripheral side surface of the first bending piece is R2, an outer dimension in the first direction in a distal-end-side cross section of the outer peripheral side surface of the second bending piece is r1 and an outer dimension in a direction orthogonal to the first direction in the distal-end-side cross section of the outer peripheral side surface of the second bending piece is r2, $(R1-r1) \times (R2-r2) < 0$.

12. An endoscope including a bending portion in which a plurality of bending pieces are arranged in an axis direction and adjacent bending pieces are coupled in a rotatable manner, the bending portion which is to be bent by operation of an internally inserted operation wire, the bending portion comprising:
- a first bending piece including a first distal end, a first proximal end, a first longitudinal axis which connects the first distal end and the first proximal end, and an outer peripheral side surface in which a proximal-end-side cross section orthogonal to the first longitudinal axis is protruding outward over a whole circumference,
- a second bending piece which is coupled with a proximal end side of the first bending piece in a rotatable manner in a first direction orthogonal to the first longitudinal axis with respect to the first bending piece, the second bending piece including a second distal end, a second proximal end, a second longitudinal axis which connects the second distal end and the second proximal end, and an outer peripheral side surface in which a distal-end-side cross section orthogonal to the second longitudinal axis is protruding outward over a whole circumference; and
- a wire clearance portion formed at least in the proximal end side of the bending piece with a largest contact angle among the first bending piece and the second bending piece,
- wherein, an outer dimension in the first direction in a proximal-end-side cross section of the outer peripheral side surface of the first bending piece is R1, an outer dimension r in a direction orthogonal to the first direction in the proximal-end-side cross section of the outer peripheral side surface of the first bending piece is R2, an outer dimension in the first direction in a distal-end-side cross section of the outer peripheral side surface of the second bending piece is r1 and an outer dimension in a direction orthogonal to the first direction in the distal-end-side cross section of the outer peripheral side surface of the second bending piece is r2, $(R1-r1)\times(R2-r2)<0$.

13. A bending portion for an endoscope, comprising:
- a first bending piece including a first distal end, a first proximal end, a first longitudinal axis which connects the first distal end and the first proximal end, and an outer peripheral side surface in which a proximal-end-side cross section orthogonal to the first longitudinal axis is protruding outward over a whole circumference; and
- a second bending piece which is coupled with a proximal end side of the first bending piece in a rotatable manner in a first direction orthogonal to the first longitudinal axis with respect to the first bending piece, the second bending piece including a second distal end, a second proximal end, a second longitudinal axis which connects the second distal end and the second proximal end, and an outer peripheral side surface in which a distal-end-side cross section orthogonal to the second longitudinal axis is protruding outward over a whole circumference,
- wherein, an outer dimension in the first direction in a proximal-end-side cross section of the outer peripheral side surface of the first bending piece is R1, an outer dimension in a direction orthogonal to the first direction in the proximal-end-side cross section of the outer peripheral side surface of the first bending piece is R2, an outer dimension in the first direction in a distal-end-side cross section of the outer peripheral side surface of the second bending piece is r1 and an outer dimension in a direction orthogonal to the first direction in the distal-end-side cross section of the outer peripheral side surface of the second bending piece is r2, $(R1-r1)\times(R2-r2)<0$,
- wherein the second bending piece is formed so that a cross-sectional shape in the plane perpendicular to the axis direction is a circular shape.

14. An endoscope including a bending portion in which a plurality of bending pieces are arranged in an axis direction and adjacent bending pieces are coupled in a rotatable manner, the bending portion which is to be bent by operation of an internally inserted operation wire, the bending portion comprising:
- a first bending piece including a first distal end, a first proximal end, a first longitudinal axis which connects the first distal end and the first proximal end, and an outer peripheral side surface in which a proximal-end-side cross section orthogonal to the first longitudinal axis is protruding outward over a whole circumference; and
- a second bending piece which is coupled with a proximal end side of the first bending piece in a rotatable manner in a first direction orthogonal to the first longitudinal axis with respect to the first bending piece, the second bending piece including a second distal end, a second proximal end, a second longitudinal axis which connects the second distal end and the second proximal end, and an outer peripheral side surface in which a distal-end-side cross section orthogonal to the second longitudinal axis is protruding outward over a whole circumference,
- wherein, an outer dimension in the first direction in a proximal-end-side cross section of the outer peripheral side surface of the first bending piece is R1, an outer dimension r in a direction orthogonal to the first direction in the proximal-end-side cross section of the outer peripheral side surface of the first bending piece is R2, an outer dimension in the first direction in a distal-end-side cross section of the outer peripheral side surface of the second bending piece is r1 and an outer dimension in a direction orthogonal to the first direction in the distal-end-side cross section of the outer peripheral side surface of the second bending piece is r2, $(R1-r1)\times(R2-r2)<0$,
- wherein the second bending piece is foil ied so that a cross-sectional shape in the plane perpendicular to the axis direction is a circular shape.

15. An endoscope including a bending portion in which a plurality of bending pieces are arranged in an axis direction and adjacent bending pieces are coupled in a rotatable manner, the bending portion which is to be bent by operation of an internally inserted operation wire, the bending portion comprising:
- a first bending piece which is one bending piece of the adjacent bending pieces and is formed so that a cross-sectional shape in a plane perpendicular to the axis direction is an elliptic shape, oval shape or flattened circular shape whose major axis direction or minor axis direction corresponds to a first direction;
- a second bending piece which is another bending piece of the adjacent bending pieces and is formed so that a cross-sectional shape in a plane perpendicular to the axis direction is a circular shape, elliptic shape, oval shape or flattened circular shape in which a length in the first direction differs from the first bending piece; and
- abutting portions in which a first end portion on a side facing the second bending piece in the first bending piece and a second end portion on a side facing the first bending piece in the second bending piece abut on each other, in at least two points when the bending portion is bent when the first bending piece rotates around a rotating axis orthogonal to the first direction with respect to the second bending piece by bending operation of the bending portion, wherein;

the first bending piece is formed so that the cross-sectional shape in the plane perpendicular to the axis direction is an elliptic shape whose minor axis direction corresponds to the first direction; and the second bending piece is formed so that the cross-sectional shape in the plane perpendicular to the axis direction is a circular shape whose diameter is longer than a length in the first direction of the elliptic shape in the first bending piece.

* * * * *